United States Patent [19]

Hall et al.

[11] Patent Number: 4,542,157

[45] Date of Patent: Sep. 17, 1985

[54] 7-OXABICYCLOHEPTANE SUBSTITUTED OXA PROSTAGLANDIN ANALOGS AND THEIR USE IN THE TREATMENT OF THROMBOLYTIC DISEASE

[75] Inventors: Steven E. Hall, Ewing Township, Mercer County; Martin F. Haslanger, Lambertville, both of N.J.

[73] Assignee: E. R. Squibb & Sons, Inc., Princeton, N.J.

[21] Appl. No.: 604,717

[22] Filed: Apr. 27, 1984

[51] Int. Cl.⁴ .................. A61K 31/34; A61K 31/557; C07D 307/00
[52] U.S. Cl. .................................... 514/469; 549/463
[58] Field of Search .................. 549/463; 424/285; 514/469

[56] References Cited

U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292  8/1982  European Pat. Off. .
2039909  8/1980  United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted oxo prostaglandin analogs are provided having the structural formula

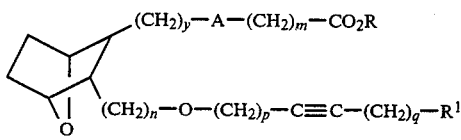

wherein R is hydrogen, lower alkyl, alkali metal or tris(hydroxymethyl)aminomethane, $R^1$ is hydrogen, lower alkyl, aryl, aralkyl, cycloalkyl or cycloalkylalkyl, A is —CH=CH— or —(CH$_2$)$_2$—, y is 0 to 4, m is 0 to 8, and n is 1 to 4, p is 1 to 12 and q is 0 to 5, and including all stereoisomers thereof.

The compounds are antiinflammatory agents useful, for example, in the treatment of inflammatory diseases and analgesic agents as well as cardiovascular agents useful, for example, in the treatment of thrombolytic disease.

17 Claims, No Drawings

7-OXABICYCLOHEPTANE SUBSTITUTED OXA PROSTAGLANDIN ANALOGS AND THEIR USE IN THE TREATMENT OF THROMBOLYTIC DISEASE

DESCRIPTION OF THE INVENTION

The present invention relates to 7-oxabicycloheptane oxaprostaglandin analogs which are antiinflammatory agents and analgesic agents and are also cardiovascular agents useful, for example, in the treatment of thrombolytic disease. These compounds have the structural formula

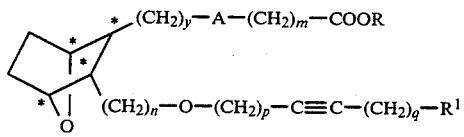

and including all stereoisomers thereof, wherein

A is $CH=CH$ or $(CH_2)_2$, y is 0 to 4, m is 0 to 8, n is 1 to 4, p is 1 to 12, q is 0 to 5, R is H, lower alkyl, alkali metal or tri(hydroxymethyl)aminomethane, and $R^1$ may be hydrogen, lower alkyl, aryl or cycloalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an aryl substitutent (that is, aralkyl), an alkoxy substituent, a haloaryl substituent, an alkyl-aryl substituent, a cycloalkyl substituent (that is, cycloalkylalkyl) or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 halogens, 1 or 2 lower alkyl groups and/or 1 or 2 lower alkoxy groups.

The term "aralkyl", "aryl-alkyl" or "aryl-lower alkyl" as used herein refers to lower alkyl groups as discussed above having an aryl substituent, such as benzyl and phenethyl.

The term "halogen" or "halo" as used herein refers to chlorine, bromine, fluorine or iodine with chlorine being preferred.

The terms "$(CH_2)_m$", "$(CH_2)_y$", "$(CH_2)_n$", "$(CH_2)_p$" and "$(CH_2)_q$" include a straight or branched chain radical having from 0 to 8 carbons in the normal chain in the case of "$(CH_2)_m$", 1 to 4 carbons in the normal chain in the case of "$(CH_2)_n$", 0-4 carbons in the normal chain in the case of "$(CH_2)_y$", 1 to 12 carbons in the normal chain in the case of "$(CH_2)_p$" and 0 to 5 carbons in the normal chain in the case of "$(CH_2)_q$" and may contain one or more lower alkyl substituents. Examples of $(CH_2)_m$, $(CH_2)_n$, $(CH_2)_p$ and $(CH_2)_q$ groups include $CH_2$,

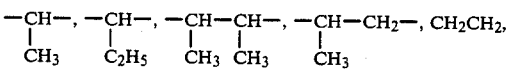

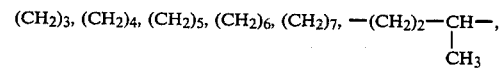

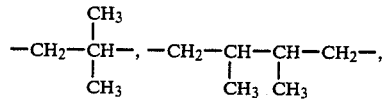

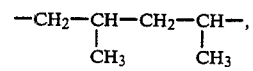

Preferred are those compounds of formula I wherein A is $(CH_2)_2$ or $CH=CH$, y is 1, m is 2 to 5, R is H, n is 1, 2 or 3, p is 1 to 8, q is 0 to 3, $R^1$ is methyl, ethyl, hydrogen, propyl, cyclohexyl, cyclohexylmethyl, phenyl, benzyl, 2-phenylethyl or 3-phenylpropyl.

The various compounds of the invention may be prepared as outlined below.

A. Where y = 1, n = 1 and A is $-CH=CH-$

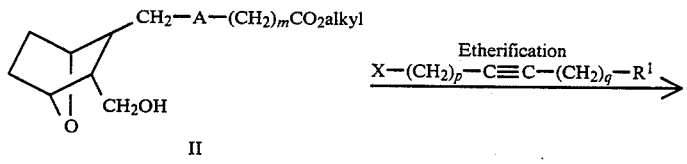

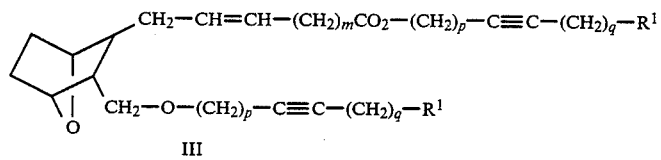

B. Where y = 1, n = 1 and A is $-(CH_2)_2-$

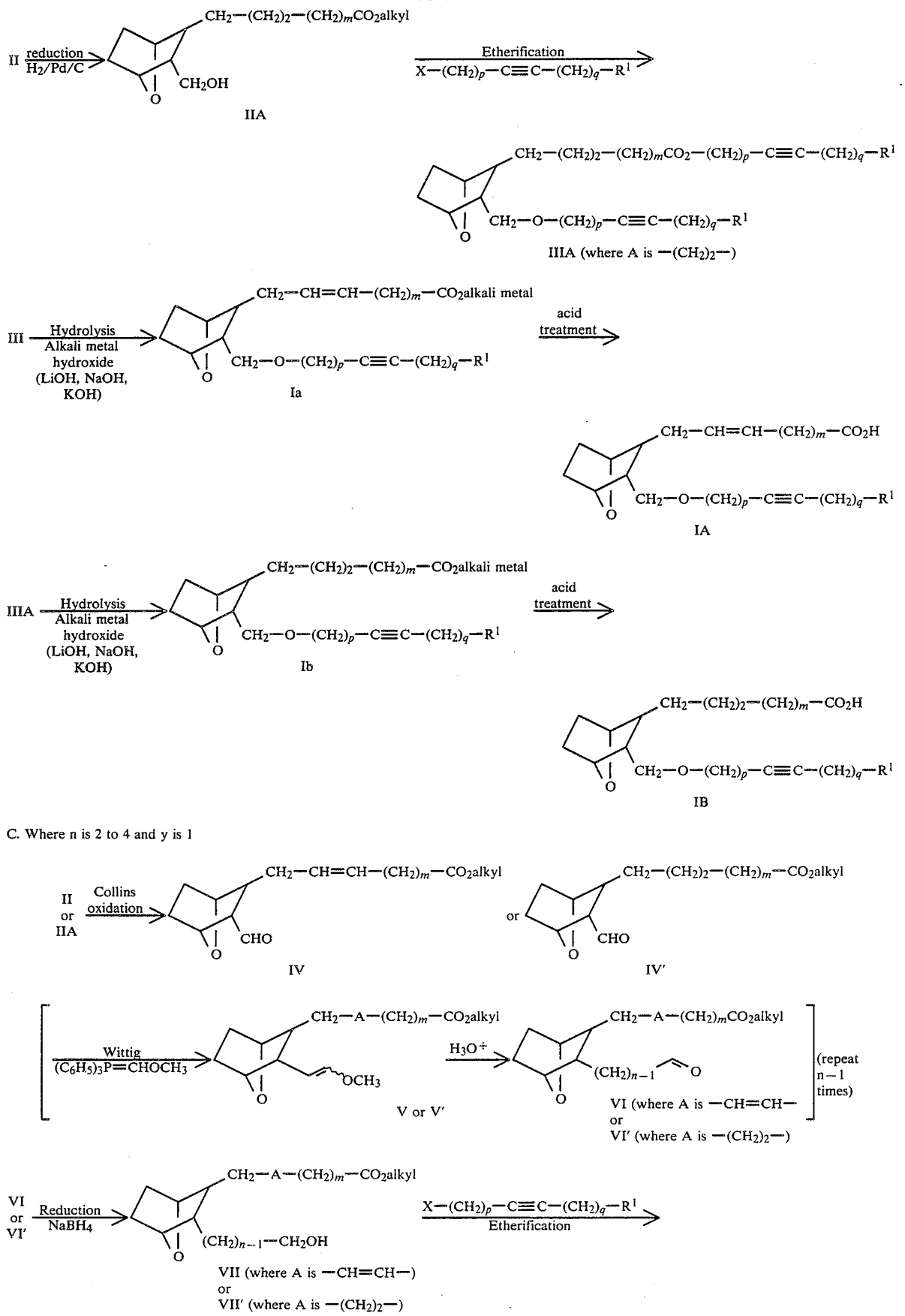

-continued
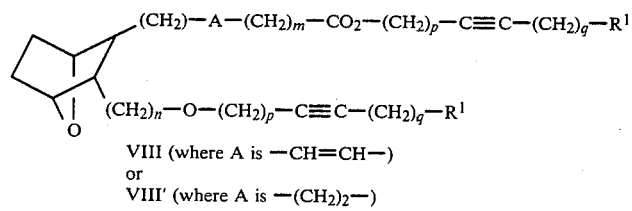
VIII (where A is —CH=CH—)
or
VIII' (where A is —(CH$_2$)$_2$—)
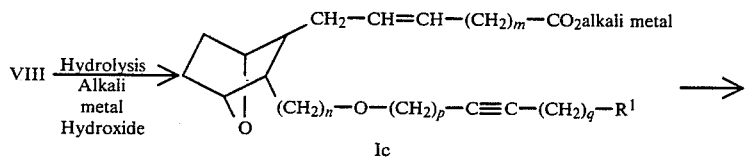
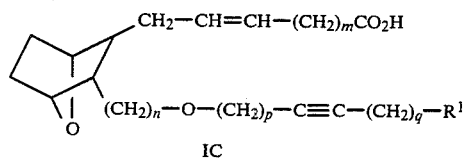
IC
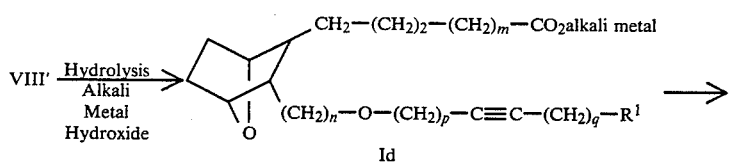
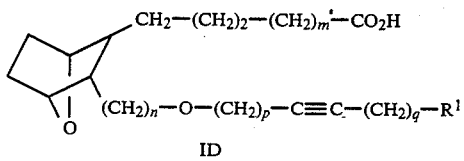
ID
D. Where y = 0, A is —CH=CH—, n is 1
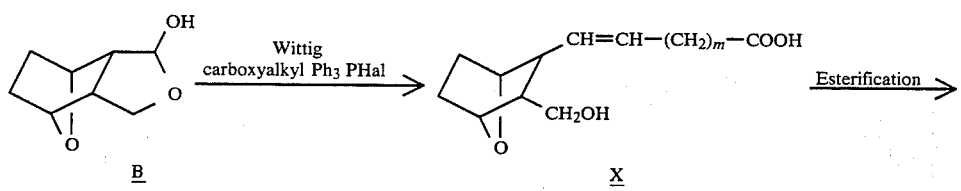
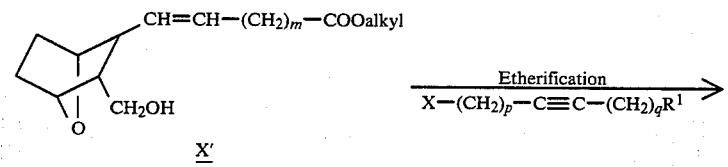
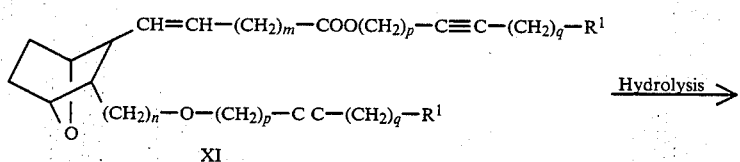

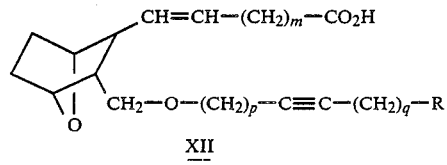
E. Where y = 0, A is —(CH$_2$)$_2$—, n is 1
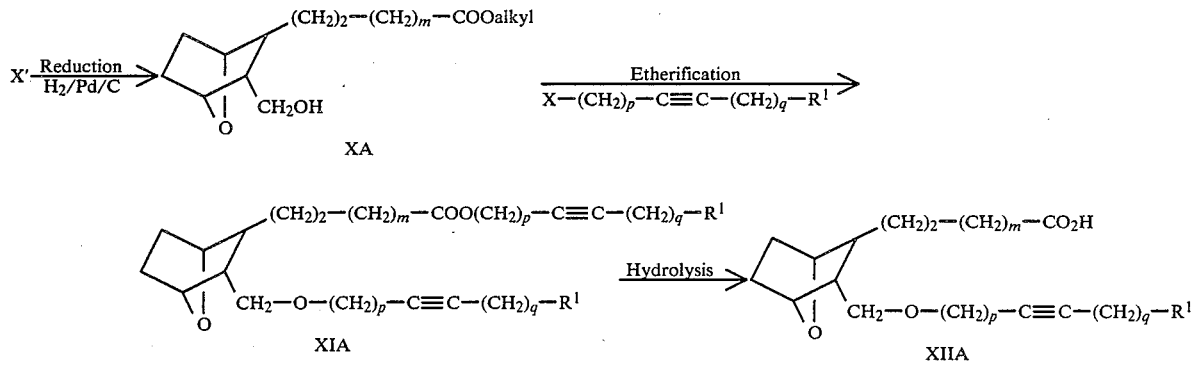
F. Where y is 2, n is 1, A is —CH=CH—
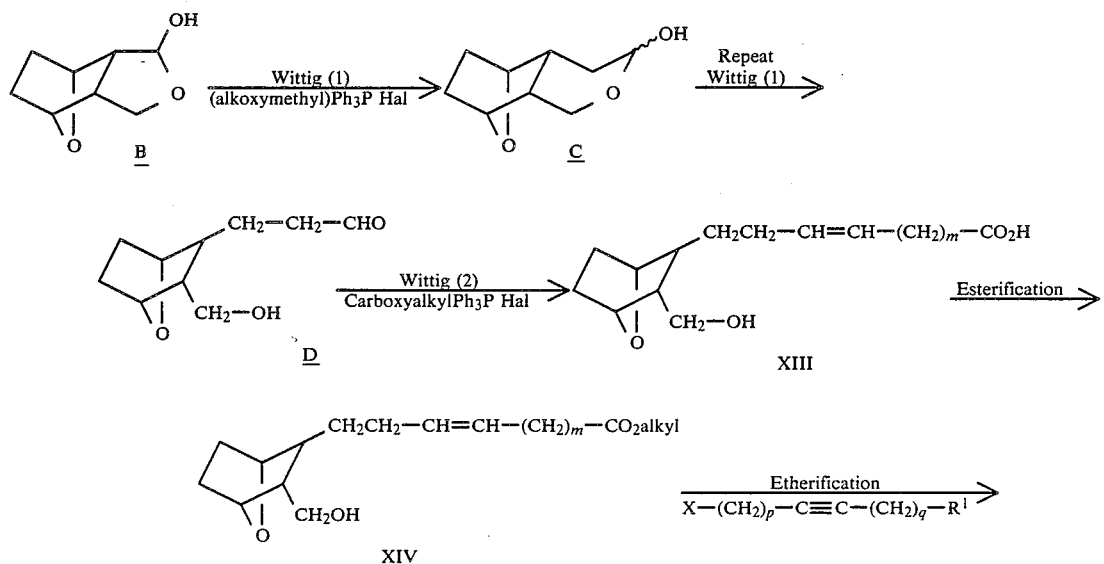
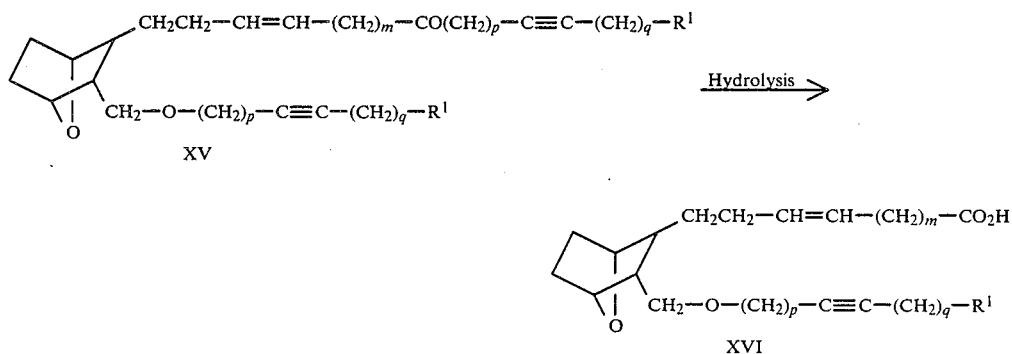
G. y is 2, n is 1, A is —CH$_2$—CH$_2$—

-continued
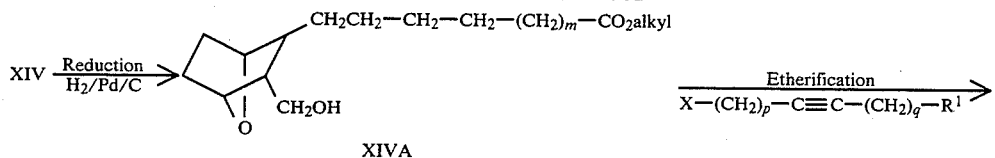
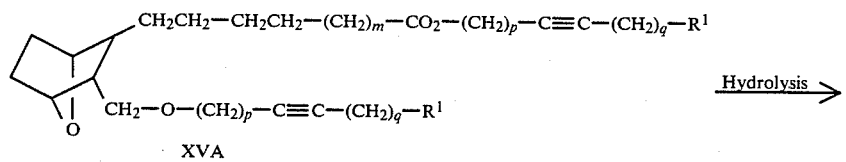
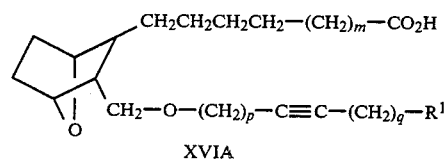
H. Where y is 3 or 4, n is 1, A is —CH=CH—
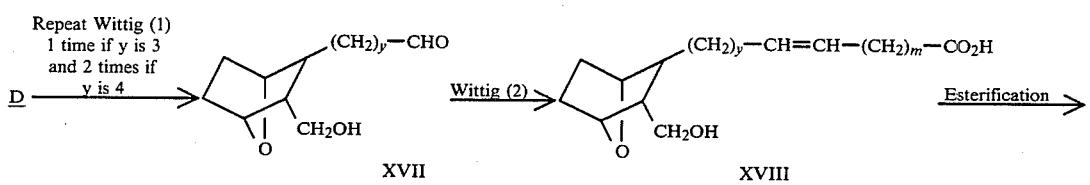
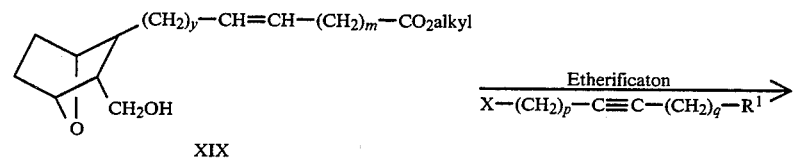
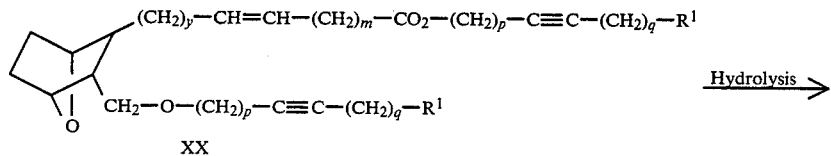
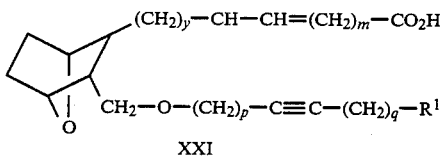
I. Where y is 3 or 4, n is 1, A is CH₂CH₂
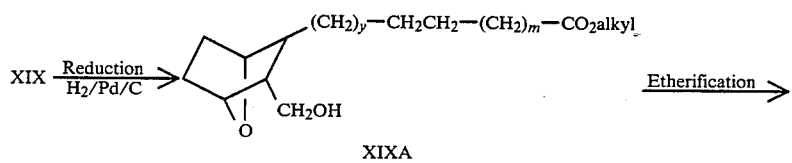
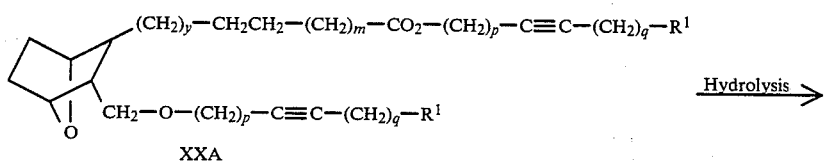

-continued

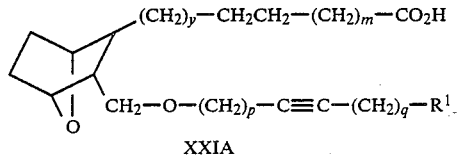
XXIA

In the reaction sequence, identified as "A", where in Formula I y is 1 and n is 1, the lower alkyl ester containing the hydroxymethyl group, that is, compound II (where A is —CH=CH—) or IIA (where A is —(CH$_2$)$_2$) (prepared as described in U.S. Pat. No. 4,143,054) is employed as the starting material. Thus, where A is —CH=CH—, compound II is subjected to an etherification reaction, for example, by reacting a compound of the structure

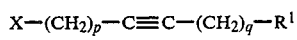   A

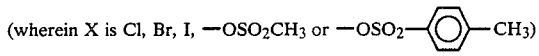

in the presence of a strong inorganic base such as KOH or NaOH, and an appropriate solvent to form ester III. To form the ester IIIA (where A is (CH$_2$)$_2$), (Reaction sequence "B"), compound II is reduced, for example, with hydrogen over a palladium on carbon catalyst, to form hydroxymethyl compound IIA (where A is (CH$_2$)$_2$) and compound IIA is subjected to an etherification reaction as described above to form ester IIIA (where A is (CH$_2$)$_2$). In carrying out the above reaction, the hydroxymethyl compound II or IIA is employed in a molar ratio to the halide A, that is, II or IIA:A, of within the range of from about 0.8:1 to about 1:5, employing a solvent such as xylene, tetrahydrofuran (THF), dimethylsulfoxide (DMSO) or dimethyl formamide (DMF). Where in the formula A starting material, X is Br or Cl, a phase transfer etherification is employed in which case THF is used as the solvent and a phase transfer reagent such as Bu$_4$NHSO$_4$, or (C$_6$H$_5$CH$_2$)(CH$_3$)$_3$NHSO$_4$ is employed.

In the reaction sequence identified as "C", where in Formula I n is 2 to 4, the starting lower alkyl ester containing the hydroxymethyl group, that is, compound II, (prepared as described in U.S. Pat. No. 4,143,054) is used to form the aldehyde IV (where A is —CH=CH—) or IV' (where A is —(CH$_2$)$_2$) Thus, to form aldehyde IV where A is —CH=CH—, compound II is subjected to a Collins oxidation, for example, by reacting II with chromium trioxide in pyridine. To form the aldehyde IV' (where A is (CH$_2$)$_2$), compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IV' (where A is (CH$_2$)$_2$).

The aldehyde IV or IV' is used to prepare aldehyde VI or VI' (where n is 2-4) carrying out a homologation sequence, such as a Wittig reaction with (C$_6$H$_5$)$_3$P=CHOMe followed by hydrolysis, (n−1) times. The aldehyde VI or VI' (where n is 2 to 4) is thus carried on to compounds of this invention where n is 2 to 4, that is VIII or VIII'.

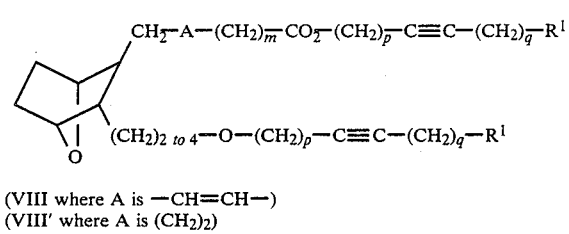

(VIII where A is —CH=CH—)
(VIII' where A is (CH$_2$)$_2$)

by reducing aldehyde VI or VI' employing a reducing agent such as sodium borohydride or sodium cyanoborohydride in a solvent such as methanol to form the alcohol ester VII or VII' which is subjected to an etherification reaction as described above to form VIII or VIII'.

Referring now to reaction sequence D, comounds of the invention wherein y is 0 and A is —CH=CH—, that is, compound XII, may be prepared by subjecting compound B (prepared as described in Example 3 of U.S. Pat. No. 4,143,054) to a Wittig reaction, for example, as described in Example 6(c) of U.S. Pat. No. 4,143,054, by reacting B with a carboxyalkyltriphenyl phosphonium halide, such as carboxypentyltriphenyl phosphonium bromide to form the hydroxymethyl compound X which after esterification to X' may then be etherified to form the ester XI which, in turn, may be hydrolyzed to the acid XII.

As seen in reaction sequence E, where it is desired to prepare compounds of the invention wherein y is 0 and A is (CH$_2$)$_2$, the hydroxymethyl compound X' is reduced by treatment with hydrogen in the presence of a palladium on carbon catalyst to form hydroxymethyl compound XA which may then be etherified to form ester XIA which then may be hydrolyzed to acid XIIA.

Compounds of the invention wherein y is 2, A is —CH=CH— and n is 1 may be prepared as outlined in reaction sequence F by subjecting starting compound B to a Wittig reaction, referred to as Wittig (1), by reacting B with an alkoxymethyltriphenyl phosphonium halide, such as (methoxymethyl)triphenylphosphonium chloride, for example, as described in Example 4 of U.S. Pat. No. 4,143,054, to form compound C. The Wittig (1) procedure is repeated on compound C to form aldehyde compound D. Aldehyde D is then subjected to a Wittig (2) procedure wherein D is reacted with a carboxyalkyltriphenylphosphonium halide, such as carboxypentyltriphenylphosphonium bromide, to form hydroxymethyl compound XIII. Compound XIII is esterified, for example, by reacting with diazomethane, to form ester XIV which is etherified as described above to form ester XV which, in turn, may be hydrolyzed to the acid XVI.

Compounds of the invention wherein y is 2, A is —CH$_2$—CH$_2$— and n is 1 may be prepared as outlined in reaction sequence G by reducing hydroxymethyl compound XIV to form compound XIVA which is then etherified to form ester XVA which is then hydrolyzed to form acid XVIA as described hereinbefore.

Referring to reaction sequence H, compounds of the invention wherein y is 3 or 4, A is —CH=CH— and n is 1 may be prepared by subjecting aldehyde D to the Wittig (1) procedure one time in the case where y is 3 and a second time in the case where y is 4, to form the aldehyde XVII. Aldehyde XVII is then subjected to the Wittig (2) procedure to form acid XVIII which is esterified to form ester XIX which is etherified as described above to form ester XX. Ester XX may then be hydrolyzed to form acid XXI.

As seen in reaction sequence I, compounds of the invention wherein y is 3 or 4, A is $CH_2CH_2$ and n is 1 may be prepared by reducing hydroxymethyl compound XIX to form compound XIXA which is then etherified to form ester XXA which, in turn, is hydrolyzed to form acid XXIA.

Compounds of the invention wherein y is 0, 2, 3 or 4 and n is 2, 3 or 4 may be prepared by substituting hydroxymethyl compound X, XA, XIV, XIVA, XIX or XIXA in place of hydroxymethyl compound II or IIA in reaction sequence C.

The esters III, IIIA, VIII or VIII', XI, XIA, XV, XVA, XX and XXA can be converted to the free acid, that is, to I (A is CH=CH)
or
I' (A is $(CH_2)_2$)

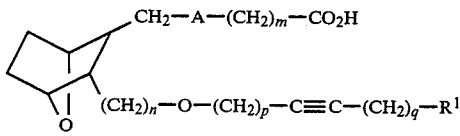

by treating the esters with an alkali metal hydroxide, such as lithium or sodium hydroxide to form the alkali metal salt Ia or Ib or Ic or Id, followed by neutralization with an acid, such as dilute hydrochloric acid or oxalic acid to form the acid IA, IB, IC or ID.

The tri(hydroxymethyl)aminomethane salt of any of the acids of formula I of the present invention is formed by reacting a solution of such acid in an inert solvent such as methanol with tri(hydroxymethyl)aminomethane and thereafter removing the solvent by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

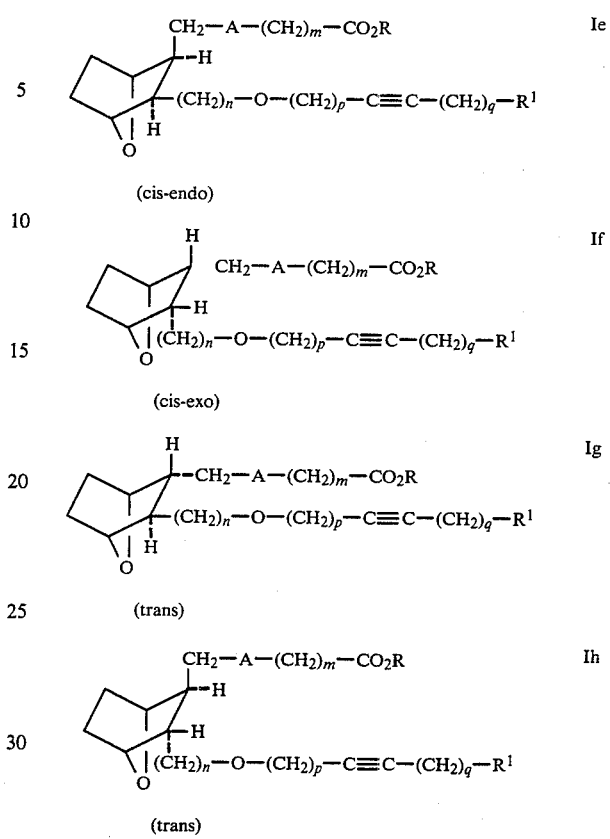

The nucleus in each of the compounds of the invention is depicted as

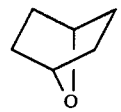

for matter of convenience; it will also be appreciated that the nucleus in the compounds of the invention may be depicted as

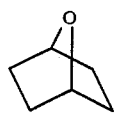

The compounds of this invention are cardiovascular agents useful as platelet aggregation inhibitors, such as in inhibiting arachidonic acid-induced platelet aggregation, e.g., for treatment of thrombolytic disease, such as coronary or cerebral thromboses, or in inhibiting broncho-constriction associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors and are useful as analgesic agents in the manner of aspirin and indomethacin. In addition, the compounds of the invention are useful as antiinflammatory agents in the manner of indomethacin and phenylbutazone as indicated by carragenin-induced edema in the rat [Ref: Winter et al, J. Pharmacol, Exp. Ther. 141:369, 1963] and they may be used to decrease joint swelling, tenderness, pain and stiffness in conditions such as rheumatoid arthritis. The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1α,2β(Z),3β,4α]-7-[3-[(2-Hexynyloxy)methyl]-7-oxabicyclo[2.2.1]hept-2-yl]-5-heptenoic acid, 2-hexynyl ester

A.

[1α,2β(Z),3β,4α]-7-[3-(Hydroxymethyl)-7-oxabicyclo[2.2.1]hept-2-yl]-5-heptenoic acid, methyl ester (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml); the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane: yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g 12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing. This was recrystallized twice from ethyl acetatecyclohexane to yield 320 mg of [1α,2β(5Z),3β,4α]-7-[3-(hydroxymethyl)-7-oxabicyclo[2.2.1]hept-2-yl]-5-heptenoic acid.

(d) Following the procedure as set out in Example 7 of U.S. Pat. No. 4,143,054, the acid from part (c) is converted to the corresponding methyl ester.

B. [1α,2β(Z),3β,4α]-7-[3-[(2-Hexynyloxy)-methyl]-7-oxabicyclo[2.2.1]hept-2-yl]-5-heptenoic acid, 2-hexynyl ester A mixture of 650 mg powdered KOH (11.6 mmol) in 19 ml of dry xylene was heated to reflux under argon atmosphere and 10 ml of xylene was removed by distillation. To this mixture was added a solution of 360 mg (1.34 mmol) of title A alcohol methyl ester in 12 ml of dry xylene. The volume of the reaction mixture was reduced 7 ml by distillative removal of xylene. To the reaction mixture was then added a solution of 1.46 g (8.3 mmol) 2-hexynyl-1-mesylate in 11 ml of dry xylene and an additional 5 ml of xylene was removed by distillation. This mixture was refluxed for 30 minutes and then allowed to cool to room temperature. The cooled reaction mixture was partitioned between 25 ml each of saturated NH$_4$Cl and EtOAc. The aqueous layer was acidified to pH 2 with 1N HCl. The aqueous layer was then extracted with two 25 ml portions of EtOAc. The combined EtOAc layers were dried (MgSO$_4$), filtered and concentrated in vacuo. Purification was effected by chromatography on 34 g of silica gel 60 using hexane:ether (4:1) as eluant. This gave 190 mg (34%) of title B ester (34%) and 190 mg (34%) of slightly impure title B ester.

EXAMPLE 2

[1α,2β(Z),3β,4α]-7-[3-[(2-Hexynyloxy)methyl]-7-oxabicyclo[2.2.1]hept-2-yl]-5-heptenoic acid A solution of 190 mg (0.46 mmol) of Example 1 ester in 3.5 ml of THF was purged with Ar. To this stirred solution was added 0.7 ml of H$_2$O and 1.4 ml of 1N LiOH. To the resulting two-phase mixture was added 1.0 ml CH$_3$OH which afforded a homogeneous mixture. This solution was stirred for 3 hours at room temperature. The reaction mixture was partitioned between 20 ml each of saturated NaCl and EtOAc. The aqueous layer was acidified with 1N HCl to pH=4 and then extracted with two 20 ml portions of EtOAc. The combined EtOAc layers were dried over MgSO4, filtered, and concentrated in vacuo to afford the crude product. Purification was effected by flash chromatography on 30 g of silica gel using 2% MeOH/CH2Cl2 as eluant to afford 126 mg of title acid (94%). TLC: silica gel, 4% CH3OH/CH2Cl2, iodine, $R_f$=0.32.

Anal. Calcd for $C_{20}H_{30}O_4$: C, 71.82; H, 9.04. Found: C, 71.66; H, 9.21.

EXAMPLE 3

[1α,2β,3β,4α]-7-[3-[(2-Hexynyloxy)methyl]-7-oxabicyclo[2.2.1]hept-2-yl]heptanoic acid, 2-hexynyl ester

A.

(1α,2β,3β,4α)-7-[3-(Hydroxymethyl)-7-oxabicyclo[2.2.1]hept-2-yl]heptanoic acid, methyl ester To 800 mg of (3.0 mmole) of the [1α,2β(Z),3β,4α]-7-[3-(hydroxymethyl)-7-oxabicyclo[2.2.1]-hept-2-yl]-5-heptenoic acid, methyl ester as prepared in Example 1, dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25° C., filtered through a celite plug and evaporated to provide 730 mg of the title A compound.

B.

(1α,2β,3β,4α)-7-[3-(2-Hexynyloxy)methyl]-7-oxabicyclo[2.2.1]hept-2-yl]heptanoic acid, 2-hexynyl ester Following the procedure of Example 1 except substituting the above Part A alcohol-ester for the Example 1A alcohol ester, the title product is obtained.

EXAMPLE 4

[1α,2β,3β,4α]-7-[3-[(2-Hexynyloxy)methyl]-7-oxabicyclo[2.2.1]hept-2-yl]heptanoic acid Following the procedure of Example 2 except substituting the Example 3 hexynyl ester for the Example 1 hexynyl ester, the title acid is obtained.

EXAMPLE 5

[1β,2α(Z),3β,4β]-7-[3-[(2-Hexynyloxy)methyl]-7-oxabicyclo[2.2.1]hept-2-yl]-5-heptenoic acid

A.

[1β,2α(5Z),3β,4β]-7-[3-(Hydroxymethyl)-7-oxabicyclo[2.2.1]hept-2-yl]-5-heptenoic acid, methyl ester To a solution of 2.68 g of Example 1, part A alcohol in 175 ml of dimethylformamide was added 13.16 g of pyridinium dichromate. This mixture was stirred at room temperature for 19 hours at which time an additional 8 g of pyridinium dichromate was added. This mixture was allowed to stir an additional 24 hours. The reaction mixture was diluted with 500 ml of ether and the resultant precipitate was removed by filtration through a pad of Celite. The filtrate was concentrated in vacuo. The resulting dark brown oil was passed through 60 g of silica gel 60 and eluted with 5% MeOH/CH2Cl2 to give 1.86 g of oil.

This was purified by chromatography on 150 g of silica gel 60 using 1:1:0.01 pentane-ether-acetic acid as eluant. This gave 0.63 g of [1β,2α(Z),3α,4β]-7-[3-(carboxy)-7-oxabicyclo[2.2.1]hept-2-yl]-5-heptenoic acid, methyl ester and 0.31 g of [1β,2α(Z),3β,4β]-7-[3-(carboxy)-7-oxabicyclo[2.2.1]hept-2-yl]-5-heptenoic acid, methyl ester; $^{13}$CNMR(CDCl3, 15.0 MHz) δ 177.0, 174.0, 130.6, 127.7, 81.5, 77.9, 54.7, 51.3, 46.2, 33.4, 32.3, 29.2, 26.6, 25.8, 24.7.

A solution of 350 mg of [1β,2α(5Z),3β,4β]-7-[3-(carboxy)-7-oxabicyclo[2.2.1]hept-2-yl]-5-heptenoic acid, methyl ester acid and 0.35 ml of triethylamine in 3.0 ml of dry THF under Ar was cooled to 0° C. To this stirred solution was added dropwise 0.24 ml of ethylchloroformate. The resulting mixture was stirred at 0° C. for 50 minutes and then diluted with 20 ml of anhydrous ether. The mixture was filtered through a pad of MgSO4 and concentrated in vacuo. The residue was dissolved in 2 ml of absolute EtOH and 3.3 ml of dry THF. This solution was cooled in an ice bath and then 80 mg of NaBH4 was added. The mixture was stirred for 30 minutes at 0° C. and then the ice bath was removed. After 15 minutes, the reaction mixture was poured into 25 ml of ice-cold 1N HCl. The aqueous layer was extracted with three 25 ml portions of ether. The ether layers were combined, dried over MgSO4, filtered, and concentrated in vacuo to afford the crude title A alcohol. Purification was effected by flash chromatography of 22 g of silica gel using 2% MeOH/CH2Cl2 as eluant. This gave 250 mg of title A alcohol; $^{13}$C NMR (CDCl3, 15.0 MHz) 6 174.1, 130.0, 128.5, 80.6, 78.7, 63.4, 51.7, 51.4, 47.8, 33.4, 32.7, 29.8, 26.6, 24.7, 23.7.

B.

[1β,2α(5Z),3β(E),4β]-7-[3-[(2-Hexynyloxy)methyl]-7-oxabicyclo[2.2.1]hept-2-yl]-5-heptenoic acid Following the procedure of Examples 1 and 2 except substituting [1β,2α(Z),3β,4β]-7-[3-(hydroxymethyl)-7-oxabicyclo[2.2.1]hept-2-yl]-5-heptenoic acid, methyl ester for [1β,2α(5Z),3α,4β]-7-[3-(hydroxymethyl)-7-oxabicyclo[2.2.1]-hept-2-yl]-5-heptenoic acid, methyl ester, the title compound is obtained.

EXAMPLE 6

[1α,2β,3β,4α]-7-[3-(5-Methyl-3-hexynyloxy)methyl-7-oxabicyclo[2.2.1]hept-2-yl]-heptanoic acid Following the procedure of Examples 3 and 4 except substituting 5-methyl-hex-3-ynyl-1-mesylate for hex-2-ynyl-1-mesylate, the title compound is obtained.

EXAMPLE 7

[1α,2β(Z),3β,4α]-7-[3-(4-Octynyloxy)methyl]-7-oxabicyclo[2.2.1]hept-2-yl]-5-heptenoic acid Following the procedure of Examples 1 and 2 except substituting oct-4-ynyl methanesulfonate for hex-2-ynyl-1-mesylate, the title compound is obtained.

EXAMPLE 8

[1α,2β(Z),3β,4α]-7-[3-(6-Phenyl-2-hexynyloxy)methyl]-7-oxabicyclo2.2.1]hept-2-yl]5-heptenoic acid Following the procedure of Examples 1 and 2 except substituting 6-phenyl-hex-2-ynylmethanesulfonate for hex-2-ynyl-1-mesylate, the title compound is obtained.

EXAMPLE 9

[1α,2β(Z),3β,4α]-7-[3-(5-Cyclohexyl-5-methyl-3-pentynyloxy)methyl]-7-oxabicyclo[2.2.1]hept-2-yl]-5-heptenoic acid Following the procedure of Examples 1 and 2 except substituting 5-cyclohexyl-5-methyl-pent-3-ynyl methanesulfonate for hex-2-ynyl-1-mesylate, the title compound is obtained.

EXAMPLE 10

[1β,2α(Z),3β,4β]-7-[3-(6-Dodecynyloxy)methyl]-7-oxabicyclo[2.2.1]hept-2-yl]-5-heptenoic acid Following the procedure of Example 5 except substituting 6-dodecynylmethanesulfonate for hex-3-ynyl-1-mesylate, the title compound is obtained.

EXAMPLE 11

(1α,2β,3β,4α)-7-[3-(10-Cyclopentyl-6-decenyloxy)methyl]-7-oxabicyclo[2.2.1]hept-2-yl]-heptanoic acid Following the procedure of Examples 3 and 4 except substituting 10-cyclopentyldec-6-ynyl methanesulfonate for hex-2-ynyl-1-mesylate, the title compound is obtained.

EXAMPLE 12

[1α,1β(Z),3β,4α]-7-[3-(5-Cyclohexyl-2-pentynyloxy)methyl]-7-oxabicyclo[2.2.1]hept-2-yl]-5-heptenoic acid Following the procedure of Examples 1 and 2 except substituting 5-cyclohexyl-pent-2-ynyl methanesulfonate for hex-2-ynyl-1-mesylate, the title compound is obtained.

EXAMPLE 13

[1α,2β(Z),3β,4α]-7-[3-[(3-Butynyloxy)methyl]-7-oxabicyclo[2.2.1]hept-2-yl]-5-heptenoic acid Following the procedure of Examples 1 and 2 except substituting 3-butynyl-1-mesylate for hex-2-ynyl-1-mesylate, the title compound is obtained.

EXAMPLE 14

(1α,2β,3β,4α)-7J-[3-[(5-Hexynyloxy)methyl]-7-oxabicyclo[2.2.1]hept-2-yl]heptanoic acid Following the procedure of Examples 3 and 4 except substituting hex-5-ynyl-1-mesylate for hex-2-ynyl-1-mesylate, the title compound is obtained.

EXAMPLE 15

[1α,2β(Z),3β,4α]-7-[3-[2-(2-Hexynyloxy)ethyl]-7-oxabicyclo[2.2.1]hept-2-yl]-5-heptenoic acid A. [1α,2β(Z),3β,4α]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C$_6$H$_5$)$_3$P+-CH$_2$OCH$_3$Cl−) and 235 ml distilled toluene (stored over molecular sieves). The resulting suspension was stirred in an ice-bath, under argon, until cold and then a 1.55 M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1α,2β(Z),3β,4α]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl]-7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.-hept-2-yl]-5-heptenoic acid, methyl ester.

Compounds (B) and (C) are each treated with trifluoroacetic acid to convert each to compound (A).

B. [1α,2β(Z), 3β,4α]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with NaBH$_4$ (0.19 g, 5 mmol) in an argon atmosphere at 0° C. After stirring at 0° for 1 hour, the reaction was quenched by addition of 2N HCl (to pH 2). The methanol was removed in vacuo and the reaction mixture was taken up in ether. The ether solution was washed with saturated KHCO$_3$, saturated NaCl and dried (MgSO$_4$). The ether was evaporated to yield the title B compound.

C. [1α,2β(Z),3β,4α]-7-[3-[2-(2-Hexynyloxy)ethyl]-7-oxabicyclo[2.2.1]hept-2-yl]-5-heptenoic acid Following the procedure of Examples 1 and 2 except substituting the above part B alcohol for the alcohol in Example 1, part A, the title compound is obtained.

EXAMPLE 16

[1β,2α(Z),3β,4β]-7-[3-[2-(2-Hexynyloxy)ethyl]-7-oxabicyclo[2.2.1]hept-2-yl]-5-heptenoic acid Following the procedure of Example 15, except substituting [1β,2α(Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 17

[1α,2β,3β,4α]-7-[3-[2-(2-Hexynyloxy)ethyl]-7-oxabicyclo[2.2.1]hept-2-yl]heptanoic acid Following the procedure of Example 16 except substituting (1α,2β,3β,4α)-7-[3-formyl-7-oxabicyclo[2.2.1]hept-2-yl]heptanoic acid, methyl ester for [1β,2α(Z),3β,4β]-7-[3-formyl-7-oxabicyclo[2.2.1]hept-2-yl]-5-heptenoic acid, methyl ester, the title compound is obtained.

EXAMPLE 18

[1α,2β(Z),3β, 4α]-7-[3-[2-(7-Phenyl-2-heptynyloxy)ethyl]-7-oxabicyclo[2.2.1]hept-2-yl]-5-heptenoic acid Following the procedure of Example 15 except substituting 7-phenylhept-2-ynyl methanesulfonate for hex-2-ynyl-1-mesylate, the title compound is obtained.

EXAMPLE 19

[1β,2α(5Z),3β,4β]-7-[3-[2-(9-Cyclopropyl-6-methyl-4-nonynyloxy)ethyl]-7-oxabicyclo[2.2.1]-hept-2-yl]-5-heptenoic acid Following the procedure of Example 16 except substituting 9-cyclopropyl-6-methyl non-4-ynyl methanesulfonate for hex-2-ynyl-1-mesylate, the title compound is obtained.

EXAMPLE 20

[1α,2β(Z),3β,4α]-7-[3-[4-(2-Hexynyloxy)butyl]-7-oxabicyclo[2.2.1]hept-2-yl]-5-heptenoic acid

A.

[1α,2β(Z),3β,4α]-7-[3-(3-Oxo)propyl-7-oxabicyclo[2.2.1]hept-2-yl]-5-heptenoic acid, methyl ester Following the procedure of Example 15, part A except substituting [1α,2β(Z),3β,4α]-7-[3-(2-oxo)ethyl-7-oxabicyclo[2.2.1]hept-2-yl]-5-heptenoic acid, methyl ester for [1α,2β(Z),3β,4α]-7-[3-formyl-7-oxabicyclo[2.2.1]hept-2-yl]-5-heptenoic acid, methyl ester, the title compound is obtained.

B.

[1α,2β(Z),3β,4α]-7-[3-(4-Oxo)butyl-7-oxabicyclo[2.2.1]hept-2-yl]-5-heptenoic acid, methyl ester Following the procedure of Example 15, part A, except substituting the aldehyde from part A above, for [1α,2β(Z),3β,4α]-7-[3-formyl-7-oxabicyclo[2.2.1]hept-2-yl]-5-heptenoic acid, methyl ester, the title B aldehyde is obtained.

C.

[1β,2α(Z),3α,4β]-7-[3-(4-Hydroxybutyl)-7-oxabicyclo[2.2.1]hept-2-yl]-5-heptenoic acid, methyl ester Following the procedure of Example 15, part B, except substituting the title B aldehyde for [1α,2β(Z),3β,4α]-7-[3-(2-oxo)ethyl-7-oxabicyclo[2.2.1]hept-2-yl]-5-heptenoic acid, methyl ester, the title C alcohol is obtained.

D.

[1α,2β(Z),3β,4α]-7-[3-[4-(2-Hexynyloxy)butyl]-7-oxabicyclo[2.2.1]-hept-2-yl]-5-heptenoic acid Following the procedure of Examples 1 and 2 except substituting the above part C alcohol for the alcohol used in Example 1, part A, the title compound is obtained.

EXAMPLE 21

[1α,2β(Z),3β,4α]-7-[3-[4-(8-Cyclohexyl-5-octynyloxy)-butyl]-7-oxabicyclo[2.2.1]hept-2-yl]-5-heptenoic acid Following the procedure of Example 20 except substituting 8-cyclohexyl oct-5-ynyl methanesulfonate, for hex-2-ynyl-1-mesylate, the title compound is obtained.

EXAMPLE 22

[1α,2β(Z),3β,4α]-7-[3-[4-(7-Phenyl-2-heptynyloxy)-butyl]-7-oxabicyclo[2.2.1]hept-2-yl]-5-heptenoic acid Following the procedure of Example 20 except substituting 7-phenylhept-2-ynyl methanesulfonate for hex-2-ynyl-1-mesylate, the title compound is obtained.

EXAMPLE 23

[1β,2β(Z),3α,4β]-7-[3-[(2-Hexynyloxy)methyl]-7-oxabicyclo[2.2.1]hept-2-yl]-5-heptenoic acid, methyl ester

A.

(1β,2α,3α,4β)-cis-exo-2-Formyl-3-isopropyloxycarbonyloxymethyl-7-oxabicyclo[2.2.1]heptane To a suspension of 11.4 g lithium aluminum hydride (300 mmole, 1.6 eq) in 400 ml of dry THF at 0° C. was added dropwise a solution of 32 g of (exo)hexahydro-4,7-epoxyisobenzofuran-1,3-dione (cis-exo-aldehyde), prepared as described in Example 1 of U.S. Pat. No. 4,143,054 (190 mmole) in 400 ml of dry THF over a period of 1 hour. The reaction mixture was stirred at 25° C. for 18 hours, cooled to 0° C. and quenched by slow addition of a saturated Na$_2$SO$_4$ solution, and filtered. The solid was washed with three 100 ml portions of CH$_2$Cl$_2$. The combined organic layer was dried over MgSO$_4$ and concentrated to give 32 g of (1β,2α,3α,4β)-cis-exo-7-oxabicyclo[2.2.1]heptane 2,3-dimethanol as a colorless solid.

To a solution of 10 g of the above diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give (1β,2α,3α,4β)-cis-exo-2-hydroxymethyl-3-chlorocarbonyloxymethyl-7-oxabicyclo[2.2.1]heptane in the form of a crude oil.

The above oil was dissolved in 30 ml of dry CH$_2$Cl$_2$ and cooled to −50° C. To this solution was added dropwise a solution of 10 ml pyridine in 10 ml CH$_2$Cl$_2$. The mixture was stirred for 10 minutes and quenched with H$_2$O. The mixture was then extracted thoroughly with CH$_2$Cl$_2$. The organic extract was dried over MgSO$_4$ and concentrated to give (1β,2α,3α,4β)-cis-exo-7-oxabicycl[2.2.1]-heptane 2,3-dimethanol carbonate as a crystalline solid (10.7 g).

A mixture of 10.7 g of the above cyclic carbonate (58.1 mmole) in 100 ml isopropanol was refluxed for 24 hours. Excess isopropanol was removed under reduced pressure to give 14.4 g (1β,2α,3α,4β)-cis-exo-2-hydroxymethyl-3-isopropyloxycarbonyloxymethyl-7-oxabicyclo[2.2.1]heptane as a viscous oil.

To a mechanically stirred suspension of 18.02 g of pyridinium chlorochromate in 112 ml of dry CH$_2$Cl$_2$ was added a solution of 12.02 g of (1β,2α,3α,4β)-cis-exo-2-hydroxymethyl-3-isopropyloxycarbonyloxymethyl-7-oxabicyclo[2.2.1]heptane in 12 ml of CH$_2$Cl$_2$ in one portion. The mixture was stirred for 90 minutes at room temperature and then diluted with 120 ml of ether. The supernatant liquid was decanted off and the gummy residue was washed with three 70 ml portions of ether. The combined organic solutions were passed through a short pad of Florosil ® and the filter cake washed with five 50 ml portions of ether. The filtrates were concentrated in vacuo to afford 10.12 g (85%) of (1β,2α,3α,4β)-cis-exo-2-formyl-3-isopropyloxycarbonyloxymethyl-7-oxabicyclo[2.2.1]heptane $^{13}$C NMR (CDCl$_3$, 15.0 MHz) δ 201.0, 154.0, 77.8, 77.1, 72.1, 65.8, 57.6, 47.3, 29.1, 28.8, 21.5.

B.
(1β,2β,3α,4β)-2-Formyl-3-isopropyloxycarbonyloxymethyl-7-oxabicyclo[2.2.1]heptane A solution of 10.12 g of the above aldehyde in 170 ml of MeOH was cooled in an ice-bath under argon. To this stirred solution was added 0.85 g of NaOCH$_3$. After 15 minutes, the ice-bath was removed and the mixture was allowed to warm to room temperature over 2 hours. The volume of the reaction mixture was reduced 50% in vacuo and then poured into 500 ml of saturated NH$_4$Cl solution. This was extracted with three 200 ml portions of ether. The combined ether extracts were washed with 200 ml of brine, dried over MgSO$_4$, filtered, and concentrated in vacuo to give 10.4 g of wet crude product. Azeotropic removal of water with CH$_2$Cl$_2$ gave 6.19 g (61%) of title compound as a mixture of the isopropyl and methyl carbonates; $^{13}$C NMR (CDCl$_3$, 15.0 MHz) δ 199.4, 154.3, 79.1, 76.6, 71.9, 68.2, 59.1, 53.2, 43.3, 28.8, 26.0, 21.5.

C.
(1β,2β,3α,4β)-2-(2-Methoxyethenyl)-3-isopropyloxycarbonyloxymethyl-7-oxabicyclo[2.2.1]heptane To a stirred slurry of 11.28 g of (methoxymethyl)triphenylphosphonium chloride at −15° C. was added dropwise 19.9 ml of 1.42 M KOt-amylate in toluene over 10 minutes. The reaction mixture was stirred 10 minutes and then placed in a 0° C. bath. To this burgundy red solution was added dropwise a solution of 5.69 g of title B aldehyde in 34 ml of THF over 2 hours, 40 minutes. The reaction mixture was allowed to warm to room temperature and stirred for 16 hours. The mixture was then cooled to −15° C. and 11.4 ml of acetaldehyde was added slowly. After stirring for 30 minutes, the mixture was poured into 250 ml of half-saturated NH$_4$Cl and extracted with three 250 ml portions of ether. The combined ether extracts were dried over MgSO$_4$, filtered, and concentrated in vacuo to afford the crude product. This was chromatographed on 150 g of silica gel using 1% CH$_3$OH, CH$_2$Cl$_2$ as eluant to give two mixed collections containing title compound C, 2.1 g and 4.2 g. The latter was triturated in hexane to give 1.62 g of the title enol ether, $^{13}$C NMR (CDCl$_3$, 15.0 MHz) δ 149.0, 148.4, 104.3, 101.0, 80.4, 79.3, 78.6, 71.7, 69.0, 68.5, 56.1, 49.9, 44.7, 29.5, 24.3, 23.9, 21.6.

D.
(1β,2β,3α,4β)-2-(Formylmethyl-3-isopropyloxycarbonyloxymethyl-7-oxabicyclo[2.2.1]heptane To a stirred solution of 3.72 g of the title C enol ether in 75 ml of THF was added 298 ml of 20% trifluoroacetic acid. After being stirred at room temperature for 6½ hours, the reaction mixture was neutralized to pH=70 with solid NaHCO$_3$. The THF was removed in vacuo and the aqueous layer was extracted with three 300 ml portions of ether. The combined ether extracts were dried over MgSO$_4$, filtered, and concentrated in vacuo to afford the crude title D aldehyde; $^{13}$C NMR (CDCl$_3$, 15.0 MHz) δ 200.5, 154.3, 78.8, 78.5, 71.8, 68.8, 49.3, 45.2, 38.8, 29.1, 23.8, 21.5.

E.
[1β,2β(Z),3α,4β]-7-[3-(Hydroxymethyl)-7-oxabicyclo[2.2.1]hept-2-yl]-5-heptenoic acid To a stirred slurry of 9.16 g of 4-(carboxybutyl)triphenylphosphonium bromide in 150 ml of toluene at −15° C. was added dropwise 26 ml of 1.42 M KOt-amylate in toluene. The cold bath was removed and on warming to room temperature an additional 1.56 ml of 1.42 M KOt-amylate in toluene was added. This was stirred for 1 hour and then a solution of 3.78 g of the above crude title D aldehyde in 30 ml of toluene was added slowly. This reaction mixture was stirred overnight at room temperature, then cooled to 0° C. and a solution of 5 ml HOAc in toluene (5 ml) was added. The resulting mixture was poured into 200 ml of saturated NH$_4$Cl and 200 ml EtOAc. The aqueous layer was acidified to pH=3.5–4.0, and extracted with three 200 ml portions of EtOAc. The combined EtOAc extracts were dried (MgSO$_4$), filtered, and concentrated in vacuo. The residue was triturated with 150 ml of isopropyl ether in an ice bath to give a sticky solid. The solution was decanted off and concentrated in vacuo to give 4.5 g of crude title E acid.

F.
[1β,2β(Z),3α,4β]-7-[3-(Hydroxymethyl)-7-oxabicyclo[2.2.1]hept-2-yl]-5-heptenoic acid, methyl ester To a solution of 4.5 g of crude title E acid in 25 ml MeOH was added 2.25 g of dried, powdered Amberlyst 15 resin. The mixture was stirred at room temperature for 3½ days, then diluted with 26 ml of ether and filtered through a pad of Celite. The Celite pad was washed repeatedly with ether. The filtrate was dried over MgSO$_4$, filtered and concentrated in vacuo to give 2.86 g crude product. Repeated chromatography of this material afforded 0.34 g of title I ester; $^{13}$C NMR (CDCl$_3$, 15.0 MHz) δ 173.9, 129.3, 128.5, 79.2, 78.9, 65.0, 52.5, 45.4, 33.2, 29.6, 28.8, 26.5, 24.5, 23.7; along with numerous impure fractions containing small amounts of the title ester.

G.
[1β,2β(Z),3α,4β]-7-[3-[(2-Hexynyloxy)methyl]-7-oxabicyclo[2.2.1]hept-2-yl]5-heptenoic acid Following the procedure of Examples 1 and 2 except substituting the title F alcohol methyl ester for Example 1 Part A alcohol methyl ester, the title product is obtained.

EXAMPLE 24

Tris(hydroxymethyl)aminomethane salt of [1α,2β(Z),3β,4α]-7-[3-[(2-Hexynyloxy)methyl]-7-oxabicyclo[2.2.1]hept-2-yl]-5-heptenoic acid A solution of the compound formed in Example 2 in methanol is treated with an equivalent amount of tri(hydroxymethyl)aminomethane. The solvent is removed by evaporation to yield the title compound.

EXAMPLES 25 AND 26

[1α,2β(6Z),3β,4α]-7-[(2-Hexynyloxy)methyl]-7-oxabicyclo[2.2.1]hept-2-yl]-6-heptenoic acid and
[1α,2α(6Z),3β,4α]-7-[3-[(2-Hexynyloxy)methyl]-7-oxabicyclo[2.2.1]hept-2-yl]-6-heptenoic acid

A.
[1α,2β(6Z),3β,4α]-7-[3-(Hydroxymethyl)-7-oxabicyclo[2.2.1]hept-2-yl]heptenoic acid and

B.
[1α,2α(6Z),3β,4α]-7-[3-(Hydroxymethyl)-7-oxabicyclo[2.2.1]hept-2-yl]heptenoic acid A slurry of carboxypentyl triphenylphosphonium bromide in THF is cooled in an ice bath and treated dropwise with 1.4 M KOt-amylate in toluene. After completion of this addition, the reaction mixture is allowed to warm to room temperature and is stirred for 6 hours. To this stirred solution is then added a solution of compound prepared as described in Example 1, Part A(b) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO₃ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title esters.

C.
[1α,2β(6Z),3β,4α]-7-[3-[(2-Hexynyloxy)methyl]-7-oxabicyclo[2.2.1]hept-2-yl]-6-heptenoic acid Following the procedure of Example 1 except substituting the title A and B esters for the Example 1 part A ester, the title compound is obtained.

EXAMPLE 27

[1α,2β(5Z),3β,4α]-7-[3-[(2-Hexynyloxy)methyl]-7-oxabicyclo [2.2.1]hept-2-yl]-5-octenoic acid A.
(1α,2β,3β,4α)-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) is chilled to 0° C. and treated dropwise with 1.4M potassium t-amylate in toluene (1910 ml, 2.67 mol) over 20 minutes. The resultant dark red solution is stirred at 0° C. for 1 hour. The mixture is then treated slowly over 5 minutes with solid hemiacetal (B) prepared as described in Example 3 of U.S. Pat. No. 4,143,054 and Example 1 Part A(b) (1.28 mol). The temperature gradually rises to 23° C. The mixture is stirred vigorously at room temperature for 90 minutes. The reaction mixture is then chilled to 0° C. and treated slowly with acetaldehyde (124 ml, 2.2 mol) over 10 minutes. The mixture is diluted with water (2500 ml) and treated with 10% hydrochloric acid to pH 7. The mixture is then extracted with ether (7×2 liters). The combined ether extracts are dried over magnesium sulfate, filtered, and the filtrates are concentrated in vacuo. The resultant mixture is treated with isopropyl ether (4 liters) and stirred overnight. The mixture is chilled to −10° C. for 90 minutes then filtered. The solids are washed thoroughly with isopropyl ether. The filtrate is concentrated in vacuo to an oily residue. This oily residue is treated with water (4000 ml) and is stirred vigorously for 2 hours. The aqueous layer is decanted and the oily residue is treated two additional times with water (2×1 liter). After the third wash, the residue solidified and is filtered. The combined aqueous triturates are concentrated in vacuo to 3.5 liters. The cloudy mixture is filtered through a bed of Celite. The filtrate is concentrated again to a volume of 2.3 liters. The cloudy solution is chilled in an ice bath and is treated slowly with concentrated hydrochloric acid (683 ml). The mixture is then stirred at room temperature for 3 hours. After this time the solution is neutralized by the slow addition of solid sodium bicarbonate (720 g). The mixture is filtered through a bed of Celite then is extracted with hexane (4×2 liters) then ethyl acetate (10×2 liters). The combined ethyl acetate extracts are dried over MgSO₄ and concentrated in vacuo. The solid residue is triturated with hexane (1 liter), filtered, and dried in vacuo to yield the desired compound (hemiacetal C in reaction sequence F). The above Wittig procedure is repeated on the hemiacetal C used in place of hemiacetal B to form the title aldehyde.

B.
[1α,2β(5Z),3β,4α]-8-[3-(Hydroxymethyl)-7-oxabicyclo[2.2.1]hept-2-yl]octenoic acid, methyl ester Following the procedure of Example 1 Part A except substituting the above title A aldehyde for the Example 1 Part A(b) compound, the title compound is obtained.

[1α,2β(Z),3β,4α]-8-[3-[(2Hexynyloxy)methyl]7-oxabicyclo[2.2.1]hept-2-yl]octenoic acid Following the procedure of Example 1 except substituting the title B ester for the Example 1 Part A ester, the title compound is obtained.

EXAMPLES 28 AND 29

[1α,2β(2E),3β,4α]-7-[3-(2-Hexynyloxy)methyl]-7-oxabicyclo[2.2.1]hept-2-yl]heptenoic acid and
[1α,1β(2Z),3β,4α]-7-[3-(2-Hexynyloxy)methyl]-7-oxabicyclo[2.2.1]hept-2-yl]heptenoic acid A.
[1α,2β,3β,4α]-5-[3-(Hydroxymethyl)-7-oxabicyclo[2.2.1]hept-2-yl]pentanal Following the procedure of Example 27 Part A, except substituting (1α,2β,3β,4α)-3-[3-(hydroxymethyl)-7-oxabicyclo[2.2.1]hept-2-yl]propionaldehyde for the hemiacetal B (see reaction sequence D or F), (1α,2β,3β,4α)-4-[3-(hydroxymethyl)-7-oxabicyclo[2.2.1]hept-2-yl]butanal is obtained. Then by repeating the procedure of Example 27 Part A on (1α,2β,3β,-4α)-4-[3-(hydroxymethyl)-7-oxabicyclo[2.2.1]hept-2-yl]butanal, the title A aldehyde is produced.

B.
[1α,2β(2E),3β,4α]-7-[3-(Hydroxymethyl)-7-oxabicyclo[2.2.1]hept-2-yl]heptenoic acid, methyl ester and C.
[1α,2β(2Z),3β,4α]-7-[3-(Hydroxymethyl)-7-oxabicyclo[2.2.1]hept-2-yl]heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title esters.

D.
[1α,2β(2E),3β,4α]-7-[3-(2-Hexynyloxy)methyl]-7-oxabicyclo[2.2.1]hept-2-yl]heptenoic acid and
[1α,2β(2Z),3β,4α]-7-[3-(2-Hexynyloxy)methyl]-7-oxabicyclo[2.2.1]hept-2-yl]heptenoic acid Following the procedure of Example 1 except substituting the title B and C esters for the Example 1 Part A ester, the title compounds are obtained.

EXAMPLE 30

[1β,2α(Z),3α,4β]-7-[3-[1-(2-Hexynyloxy)ethyl]-7-oxabicyclo[2.2.1]hept-2-yl]-5-heptenoic acid, 2-hexynyl ester

A.

[1β,2α(Z),3α,4β]-7-[3-[1-(hydroxy)ethyl]-7-oxabicyclo[2.2.1]hept-2-yl]5-heptenoic acid, methyl ester To a stirred solution of 1.31 g (4.91 mmol) of [1β,2α(Z),3α,3β]-7-(3-formyl-7-oxabicyclo]2.2.1]hept-5-en-2-yl]-5-heptenoic acid, methyl ester, prepared as described in U.S. Pat. No. 4,143,054 at −78° C. under argon atmosphere was added 1.64 ml of 3M CH$_3$MgBr dropwise in a period of 10 minutes. The reaction mixture was stirred for 5 minutes and the acetone-dry ice bath was removed. The reaction mixture was stirred for another 12 minutes and quenched with 1 ml of CH$_3$OH. The reaction mixture was then poured into 20 ml of saturated NH$_4$Cl solution and diluted with a solution of 40 ml of H$_2$O and 40 ml of saturated NH$_4$Cl solution. The aqueous layer was extracted with ether (3×100 ml). The combined ether extracts were dried (MgSO$_4$), filtered and concentrated in vacuo to give 1.58 g of the title alcohol methyl ester which was used as is without further purification. TLC: silica gel, 4% CH$_3$OH/CH$_2$Cl$_2$, R$_f$=0.25, iodine.

B.

[1β,2α(Z),3α,4β]-7-[3-[1-(2-Hexynyloxy)ethyl]7-oxabicyclo[2.2.1]hept-2-yl]-5-heptenoic acid, 2-hexynyl ester Following the procedure of Examples 1 and 2 except substituting the above Part A alcohol for the Example 1 Part A alcohol, the title compound is obtained.

EXAMPLES 31 TO 45

Following the procedure as described in the specification and working Examples, the following additional compounds including all isomers thereof may be prepared.

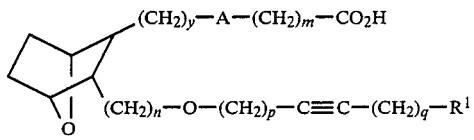

| Ex. No. | y | A | m | n | p | q | R$^1$ |
|---|---|---|---|---|---|---|---|
| 31. | 1 | (CH$_2$)$_2$ | 1 | 1 | 2 | 0 | C$_5$H$_{11}$ |
| 32. | 2 | CH=CH | 2 | 2 | 4 | 2 | C$_2$H$_5$ |
| 33. | 3 | (CH$_2$)$_2$ | 3 | 4 | 6 | 0 | C$_6$H$_5$ |
| 34. | 4 | CH=CH | 0 | 3 | 8 | 4 | C$_6$H$_5$CH$_2$— |
| 35. | 0 | (CH$_2$)$_2$ | 8 | 2 | 10 | 0 | ⬡ |
| 36. | 1 | CH=CH | 7 | 1 | 12 | 5 | ⬠-CH$_2$— |
| 37. | 2 | (CH$_2$)$_2$ | 6 | 3 | 7 | 3 | C$_6$H$_{13}$ |
| 38. | 3 | CH=CH | 5 | 4 | 5 | 1 | C$_2$H$_5$ |
| 39. | 4 | (CH$_2$)$_2$ | 0 | 1 | 3 | 4 | C$_6$H$_5$(CH$_2$)$_2$— |
| 40. | 0 | CH=CH | 2 | 1 | 1 | 2 | CH$_3$ |
| 41. | 4 | CH=CH | 3 | 2 | 1 | 3 | CH$_3$ |
| 42. | 3 | (CH$_2$)$_2$ | 4 | 3 | 2 | 2 | ⬡ |
| 43. | 2 | (CH$_2$)$_2$ | 0 | 4 | 2 | 0 | C$_6$H$_5$ |
| 44. | 1 | (CH$_2$)$_2$ | 2 | 2 | 3 | 2 | C$_2$H$_5$ |
| 45. | 1 | (CH$_2$)$_2$ | 2 | 3 | 3 | 3 | C$_6$H$_5$CH$_2$ |

What is claimed is:

1. A compound having the structural formula

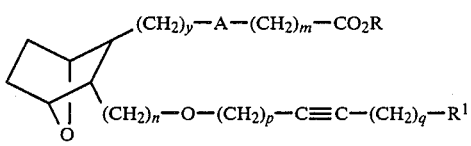

and including all stereoisomers thereof, wherein
A is —CH=CH—, or —(CH$_2$)$_2$—;
y is 0 to 4; m is 0 to 8; n is 1 to 4; p is 1 to 12; q is 0 to 5;
R is hydrogen, lower alkyl, alkali metal or tri(hydroxymethyl)aminomethane; and R$^1$ is hydrogen, lower alkyl, aryl, aralkyl, cycloalkyl or cycloalkylalkyl, wherein the term lower alkyl or alkyl by itself or as part of another group contains 1 to 12 carbons and is unsubstituted or substituted with halo, trifluoromethyl, aryl, alkoxy, haloaryl, alkyl-aryl cycloalkyl or alkylcycloalkyl;
the term aryl by itself or as part of another group contains 6 to 10 carbons and is unsubstituted or substituted with 1 or 2 lower alkyl groups, 1 or 2 halogens and/or 1 or 2 lower alkoxy groups;
the term cycloalkyl by itself or as part of another group contains 3 to 12 carbons and is unsubstituted or substituted with 1 or 2 halogens, 1 or 2 lower alkyl groups and/or 1 or 2 lower alkoxy groups;
the term (CH$_2$)$_m$ includes 0 to 8 carbons in the normal chain, the term (CH$_2$)$_n$ includes 1 to 4 carbons in the normal chain, the term (CH$_2$)$_y$ includes 0 to 4 carbons in the normal chain, the term (CH$_2$)$_p$ includes 1 to 12 carbons in the normal chain, and the term (CH$_2$)$_q$ includes 0 to 5 carbons in the normal chain; and the terms (CH$_2$)$_y$, (CH$_2$)$_m$, (CH$_2$)$_n$, (CH$_2$)$_p$ and (CH$_2$)$_q$ may be unsubstituted or include one or more lower alkyl substituents.

2. The compound as defined in claim 1 wherein A is —CH=CH—.

3. The compound as defined in claim 1 wherein R is H.

4. The compound as defined in claim 1 wherein n is 1.

5. The compound as defined in claim 1 wherein n is 2, 3 or 4.

6. The compound as defined in claim 1 wherein p is 1 and (CH$_2$)$_q$—R$^1$ is lower alkyl.

7. The compound as defined in claim 1 wherein A is —CH=CH—, y is 1, m is 2 to 4, n is 1 or 2, p is 1 or 2, q is 1 or 2, R is H, and R$^1$ is lower alkyl or cycloalkyl.

8. The compound as defined in claim 1 wherein A is —CH=CH—, m is 3, n is 1, p is 1, q is 1, R is H or 2-hexynyl, and R$^1$ is lower alkyl.

9. The compound as defined in claim 1 having the name [1α,2β(Z), 3β,4α]-7-[3-[(2-hexynyloxy)methyl]-7-oxabicyclo[2.2.1]hept-2-yl]-5-heptenoic acid or its 2-hexynyl ester, including all stereoisomers thereof.

10. A method of inhibiting platelet aggregation and bronchoconstriction, which comprises administering to the circulatory system of a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting platelet aggregation and bronchoconstriction comprising an effective amount of a compound as defined in claim 1 or a pharmaceutically acceptable salt thereof, and a pharmaceutically acceptable carrier thereof.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, which comprises administering to a mammalian host an effective amount of a compound as defined in claim 1 or a pharmaceutically acceptable salt thereof.

15. A method for inhibiting platelet aggregation and bronchoconstriction by inhibiting production of thromboxane $A_2$ by blocking the action of thromboxane synthetase, which comprises administering to a mammalian host an effective amount of a compound as defined in claim 1 or a pharmaceutically acceptable salt thereof.

16. A method for treating inflammation in a mammalian species in need of such treatment, which comprises administering to a mammalian host an effective amount of a compound as defined in claim 1 or a pharmaceutically acceptable salt thereof.

17. A method of relieving pain in a mammalian species which comprises administering to said mammalian species a composition containing an analgesically effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,542,157
DATED : September 17, 1985
INVENTOR(S) : Steven E. Hall et al.

It is certified that error appears in the above-identified patent and that said Letters Patent is hereby corrected as shown below:

Column 2, after the structure on line 37, insert --and the like--
Column 14, structure If should read -- 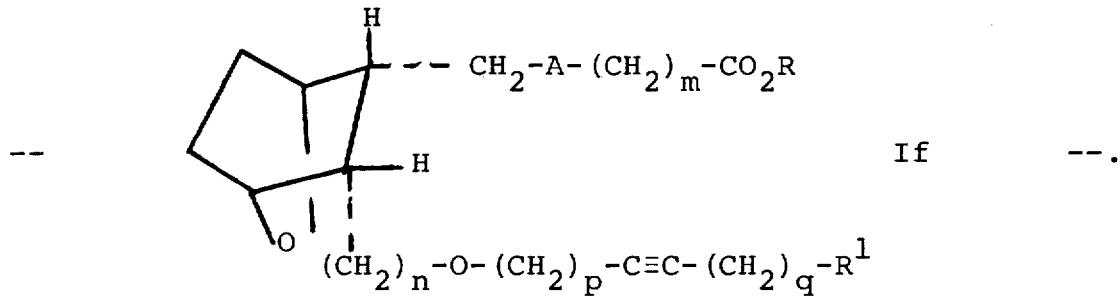 If --.

(cis exo)

Column 18, line 23, "MHz) 6" should read --MHz) $\delta$--.

Signed and Sealed this

Eleventh Day of November, 1986

Attest:

DONALD J. QUIGG

Attesting Officer  Commissioner of Patents and Trademarks